United States Patent [19]
van der Bruggen et al.

[11] Patent Number: 5,952,228
[45] Date of Patent: Sep. 14, 1999

[54] ISOLATED CYTOLYTIC T CELLS WHICH ARE SPECIFIC FOR COMPLEXES OF HLA-B35 MOLECULES AND THE PEPTIDE PHE PRO SER ASP SER TRP CYS TYR PHE, AND USES THEREOF

[75] Inventors: Pierre van der Bruggen; Susanna Mandruzzato; Thierry Boon-Falleur, all of Brussels, Belgium

[73] Assignee: Ludwig Institute for Cancer Research, New York, N.Y.

[21] Appl. No.: 09/059,964

[22] Filed: Apr. 14, 1998

Related U.S. Application Data

[60] Division of application No. 08/718,964, Sep. 26, 1996, which is a continuation-in-part of application No. 08/669,590, Jun. 24, 1996, abandoned.

[51] Int. Cl.⁶ .............................. C12N 15/85; C07K 7/06
[52] U.S. Cl. .................. 435/372.3; 435/7.24; 514/15; 514/16
[58] Field of Search ...................... 514/15, 16; 435/7.24, 435/372.3

[56] References Cited

FOREIGN PATENT DOCUMENTS

92/08806  5/1992  WIPO .

OTHER PUBLICATIONS

Fernandes–Alnemri et al., "In vitro activation of CPP32 and Mch 3by Mch 4, A Novel Human Apoptotic Cysteine Protease Containing Two FADD–like Domains", Proc. Natl. Acad. Sci. USA 93: 7464–7469 (Jul. 96).

Fraser et al., "A License To Kill", Cell 85: 781–784 (Jun. 14,1996).

Boldin et al., Involvement of MACH, a Novel MORT 1/FADD–interacting Protease in Fas/APO–and TNF Receptor Induced Cell Death, Cell 85: 803–815 1996.

Muzio, et al., "FLICE, A Novel FADD–Homologous ICE/CED–3–like Protease Is Recruited To The CD95 (Fas/APO01) Death Inducing Signaling Complex", Cell 85: 817–827 (June 14, 1996).

Schönbach, et al., "Fine Tuning of Peptide Binding to HLA–B*3501 Molecules By Nonanchor Residues", J. Immunol. 154: 5951–5958 (1995).

Ramensee, et al., "MHC Ligands And Peptide Motifs: First Listing"Immunogentics 41: 178–228 (1995).

Seite et al., "Peptide Binding To The Most Frequent HLA–A Class I Alleles Measured By quantitative Molecular Binding Assays", Mol. Immunol. 31(11): 813–822 (1994).

*Primary Examiner*—Christina Y. Chan
*Assistant Examiner*—Martha Lubet
*Attorney, Agent, or Firm*—Fulbright & Jaworski, LLP.

[57] ABSTRACT

The invention relates to isolated cytolytic T cells which recognize complexes of HLA-B35 molecules and the peptide defined by SEQ ID NO: 2, as well as methods for identifying HLA-B35 positive cells. The method involves contacting the cytolytic T cells to a sample, and determining activity of these cytolytic T cells.

2 Claims, 6 Drawing Sheets

ISOLATED CYTOLYTIC T CELLS WHICH ARE SPECIFIC FOR COMPLEXES OF HLA-B35 MOLECULES AND THE PEPTIDE PHE PRO SER ASP SER TRP CYS TYR PHE, AND USES THEREOF

RELATED APPLICATION

This application is a divisional of allowed U.S. application Ser. No. 08/718,964, filed Sep. 26, 1996, now pending, which is a continuation-in-part of application Ser. No. 08/669,590 filed Jun. 24, 1996, now abandoned.

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen that is presented by HLA-B35 molecules. The gene in question does not appear to be related to other known tumor rejection antigen precursor coding sequences, but appears to be related to members of the cysteine protease family, a group of proteins associated with cell apoptosis. The invention also relates to peptides presented by the HLA-B35 molecules, and uses thereof.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLAs"), or major histocompatibility complexes ("MHCs"), and peptides. The peptides are derived from larger molecules which are processed by the cells which also present the HLA/MHC molecule. See in this regard Male et al., Advanced Immunology (J.P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992). Also see Engelhard, Ann. Rev. Immunol. 12: 181–207 (1994).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774.

In U.S. patent application Ser. No. 938,334, now U.S. Pat. No. 5,405,940, the disclosure of which is incorporated by reference, it is explained that the MAGE-1 gene codes for a tumor rejection antigen precursor which is processed to nonapeptides which are presented by the HLA-A1 molecule. The reference teaches that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 now U.S. Pat. No. 5,629,165, and incorporated by reference, the fact that the MAGE-1 expression product is processed to a second TRA is disclosed. This second TRA is presented by HLA-C clone 10 molecules. The disclosure shows that a given TRAP can yield a plurality of TRAs.

U.S. patent application Ser. No. 994,928, filed Dec. 22, 1992, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993, now U.S. Pat. No. 5,620,866, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 Now U.S. Pat. No. 5,571,711, and incorporated by reference herein, an unrelated tumor rejection antigen precursor, the so-called "BAGE" precursor is described. The BAGE precursor is not related to the MAGE family.

The work which is presented by the papers, patents, and patent applications cited supra deals, in large part, with the MAGE family of genes, and the unrelated BAGE gene. None of this work describes a tumor rejection antigen presented by HLA-B35 molecules. Given the diversity of human MHC molecules, there is standing interest in identifying such molecules. The nucleic acid molecule which encodes the protein which is processed to this tumor rejection antigen does not appear to be related to previously identified tumor rejection antigen precursor encoding sequences; rather it appears to be related to ICE cysteine protease encoding sequences. The proteins are associated with cell apoptosis. The nucleic acid molecule (SEQ ID NO: 1), and the tumor rejection antigen (SEQ ID NO: 2), are features of the invention, which is set forth in the disclosure which follows.

DETAILED DESCRIPTION OF PREFERRED EMBODIMENTS

EXAMPLE 1

A head and neck squamous cell carcinoma referred to as BB49-SCCHN was derived from a patient tumor mass, resected, and adapted for culture. The cells were then transfected, using the well known calcium phosphate precipitation method with the expression vector pEFBOSpuro. This vector was prepared by inserting a puromycin resistance gene into plasmid pEFBOS, as described by Mizushima et al, Nucl. Acids Res. 18(17): 5322 (1990), incorporated by reference. This plasmid contains a nucleic acid sequence which encodes the human costimulatory molecule B7.1, also known as CD80. Transfectants were selected using 0.5 µg/ml of puromycin, and then cloned using limiting dilution. A clone referred to as "BB49-B7.1 clone 7" was selected on the basis of high B7.1 expression, as determined by cytofluorometric analysis, using a known anti-CD80 monoclonal antibody. This clone, and BB49-SCCHN cells, were grown in Iscove's medium augmented with 10% fetal calf serum (FCS), L-arginine (116 mg/ml), L-asparagine (36 mg/ml), L-glutamine (216 mg/ml) and ACL-4, as described by Gazdar et al., Canc. Res. 46: 6011 1986), incorporated by reference in its entirety. Peripheral blood mononuclear cells ("PBMCs" hereafter), were also isolated from the patient who provided BB49-SCCHN. The cells of patient BB49 were tested via serology, and were found to be HLA-A2, B35, B62, Cw1 and Cw4 positive.

EXAMPLE 2

Once cells were established, autologous mixed lymphocyte tumor cell culture (MLTC) assays were carried out. Specifically, on day 0, 2×10$^6$ PBMCs were stimulated with 10$^5$ irradiated BB49. B7 tumor cells (100 Gy), in 2 ml of the medium discussed supra, but without ACL-4, supplemented with 10% pooled human serum rather than FCS.

On day 3, interleukin-2 (IL-2), was added at 25 U/ml. The responding population was restimnulated on day 7 and on day 15, with 10$^5$ irradiated BB49. B7 tumor cells, in medium containing 25 U/ml of IL-2. On day 21, CD8$^+$ cells were sorted, using well known techniques. Briefly, anti-human CD8 specific monoclonal antibodies were coupled to magnetic microbeads, and then the beads were added to the sample. The CD8$^+$ cells adhered, and CD8$^+$/CD8$^-$ cells were separated via passage through a separation column. A total of 3×10$^5$ CD8$^+$ lymphocytes were then restimulated with 5×10$^4$ irradiated BB49. B7 tumor cells, and 10$^6$ irradiated (30 Gy) CD8$^-$ cells, in the presence of 25 U/ml of IL-2.

Following this, CD8$^+$ CTL clones were isolated, using limiting dilution techniques on the MLTC population, on day 28. The cytolytic activity of the CTL clones was tested in a $^{51}$Cr release assay, using BB49-SCCHN cells as targets. The targets were either pretreated for 72 hours with 100 U/ml of IFN-γ, or were untreated.

Figure 1:
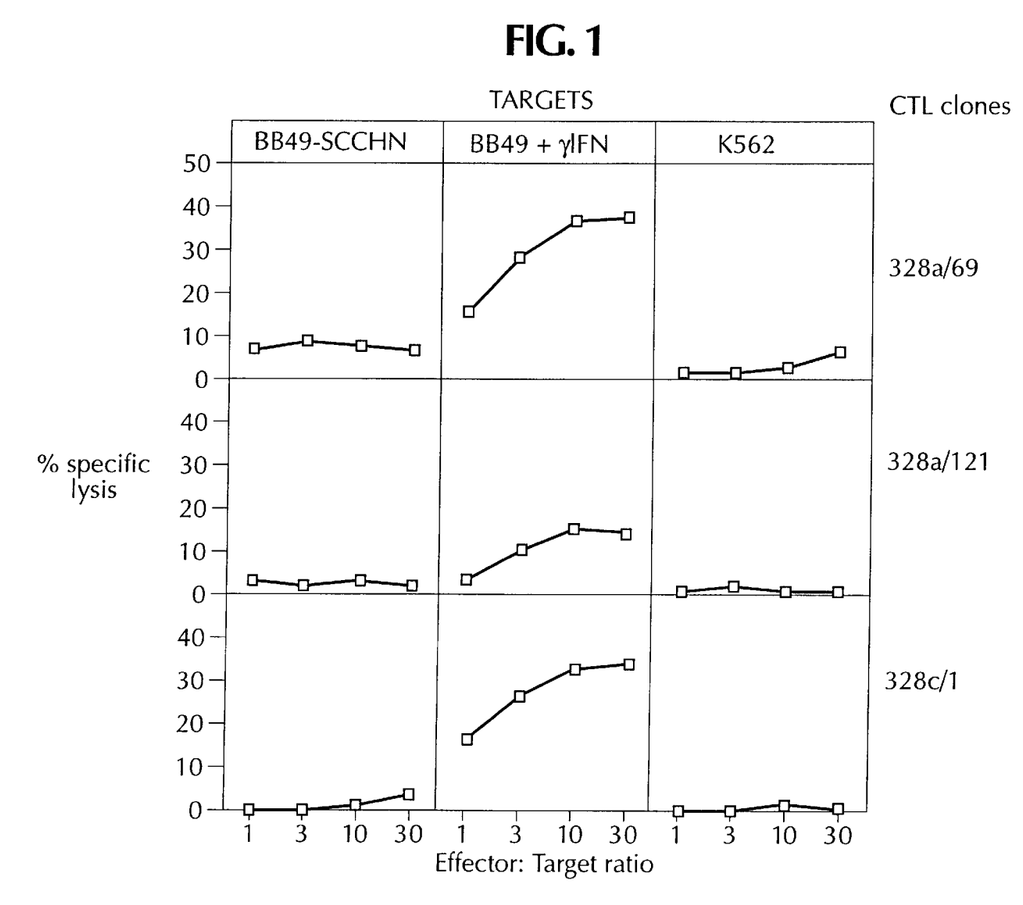
FIG. 1 shows the results obtains in studies of lytic activity of various CTL clones on targeted cell populations.

Three CTL clones which lysed BB49 were identified, which did not lyse a control sample of NK-sensitive target cells, i.e., K562 cells. These clones are referred to as CTL clones 328a/69, 328a/121, and 328c/1. FIG. 1 displays the results of experiments showing percentage of lysis of the target cells, at various effector: target ratios.

The CTL clones were then tested to see if they would release TNF when stimulated with BB49 tumor cells. This assay was carried out by mixing 10$^4$ target cells, 1500 CTLs in microwells together with 100 ul Iscove's medium with 10% human serum, and 25 U/ml of IL-2. Supernatants were collected after 4 or 24 hours, and TNF content was determined by using TNF sensitive cells, WEHI-164 clone 13.

Figure 2:
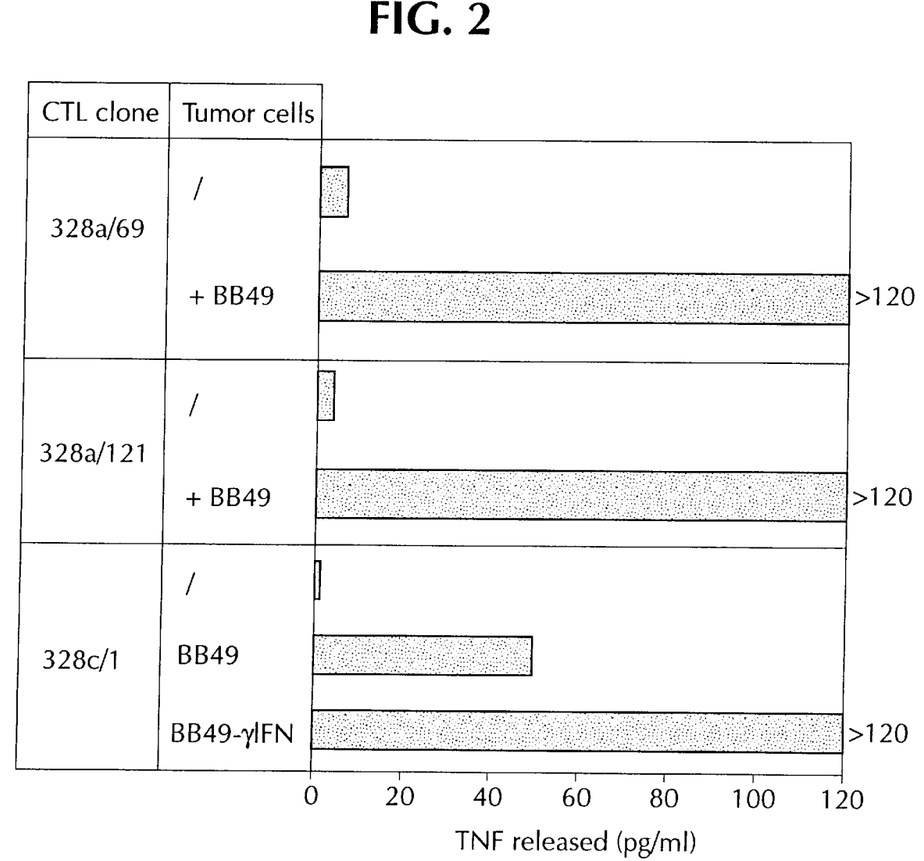
FIG. 2 depicts TNF release assays, using the same CTL clones.

FIG. 2 shows that all three CTL clones released significant amounts of TNF.

EXAMPLE 3

It was of interest to determine which HLA molecule presented antigenic peptides to the CTL clones. The CTL clone 328a/121 was used in these experiments. This involved mixing 1500 CTLs with 1–2×10$^4$ BB49 cells, and different monoclonal antibodies, which are well known to the art. W6/32 is an anti HLA-A, B, C mAb, B.1.23.2 is an anti HLA-B,C, mAb 2B5 is an anti-HLA-DR mAb (negative control), and 4E is an anti-HLA-B mAb.

Figure 3:
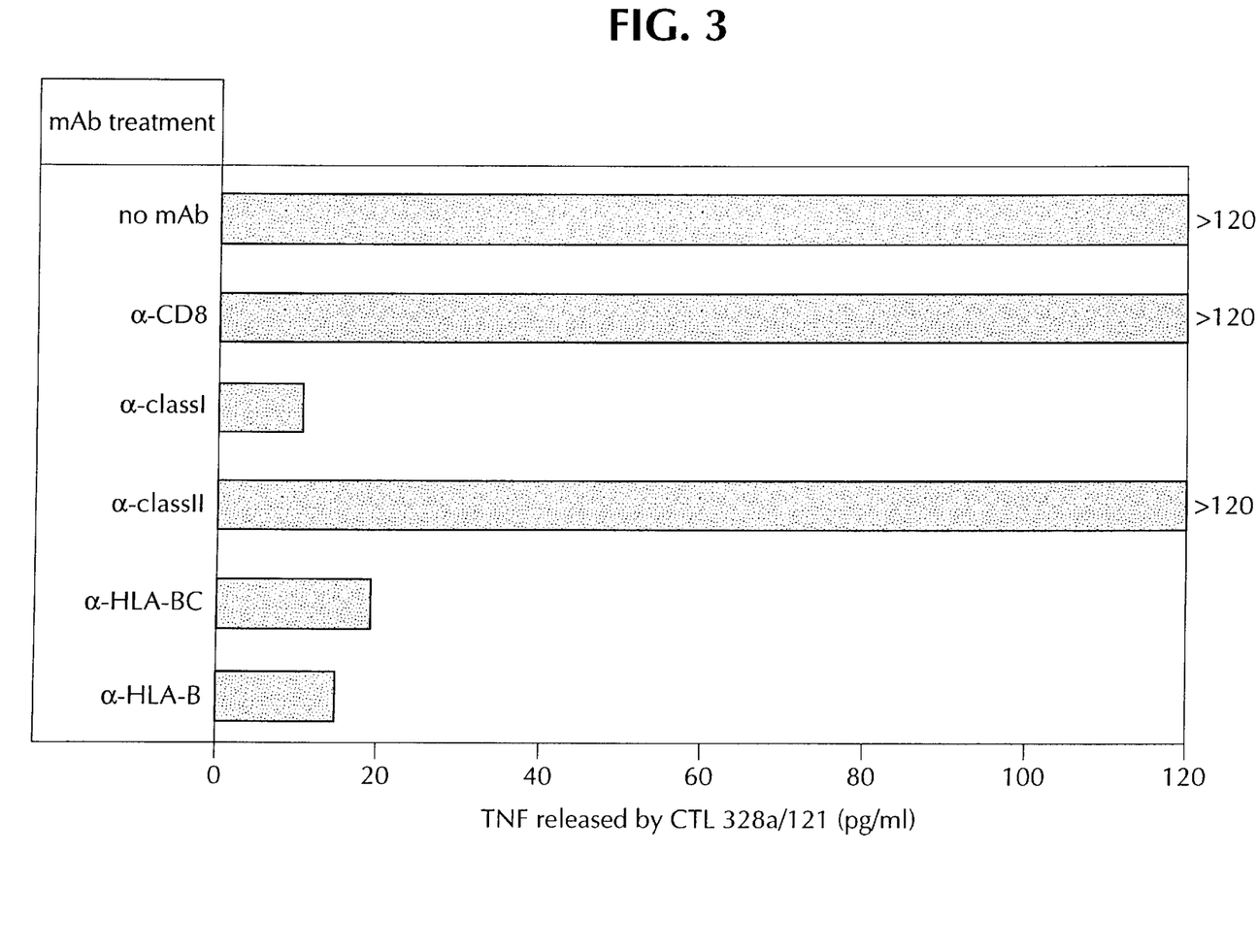
FIG. 3 displays TNF release assays carried out to determine which HLA molecule presents the antigen targeted by the CTLs.

FIG. 3 presents these results, and shows that TNF production was severely curtailed in the presence of W6/32, B.123.2 and 4E, but not 2B6, indicating recognition of an HLA-B35 or B62/peptide complex.

Figure 4:
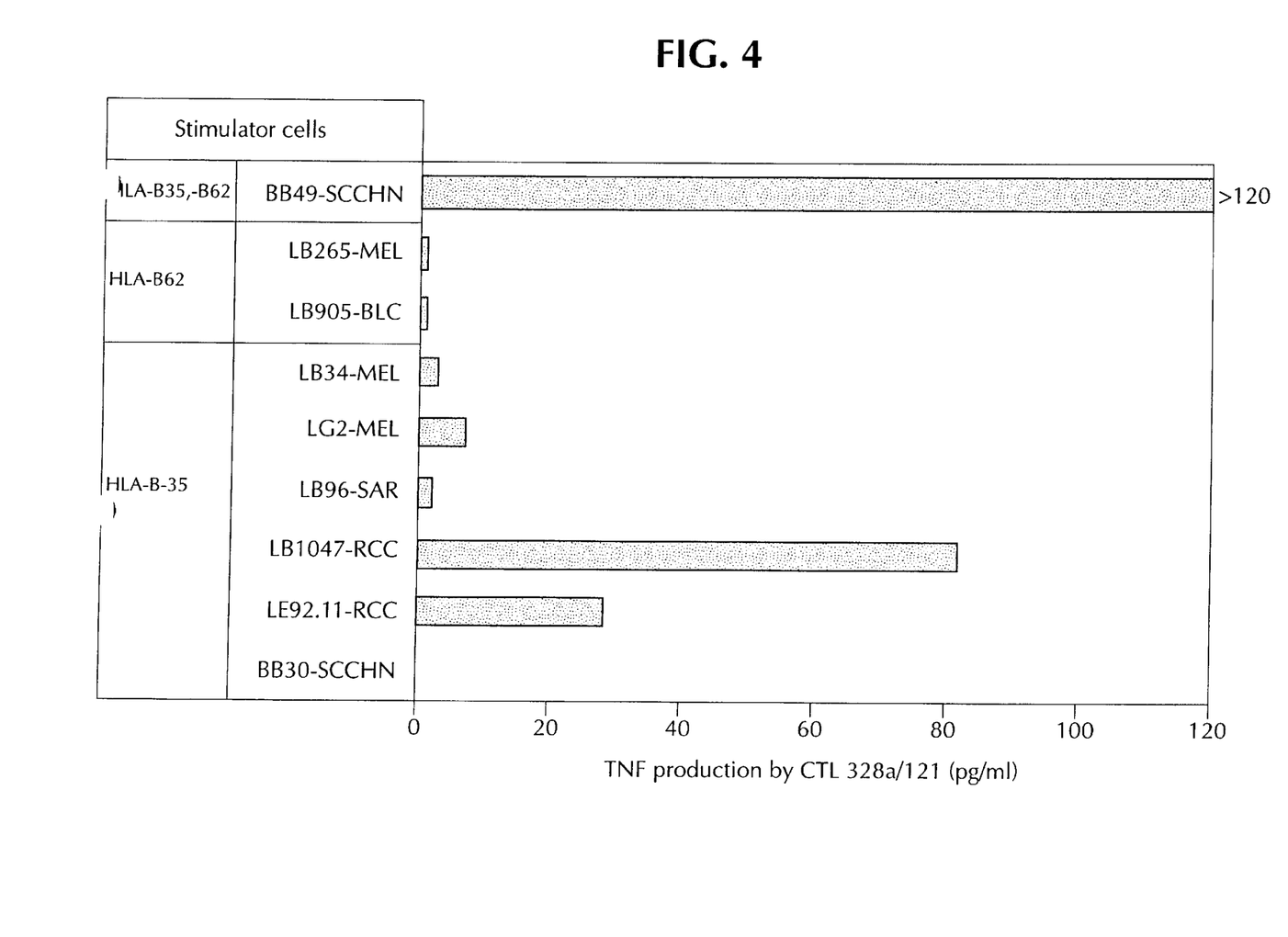
FIG. 4 shows studies designed to delineate the relevant HLA molecule with more particularity.

In order to determine which HLA molecule was involved, different HLA-B35 and HLA-B62 positive tumor cell lines were tested. FIG. 4 presents these results. LB1047-RCC and LE92.11-RCC are both HLA-B35 positive, and the results suggest that HLA-B35 is the presenting molecule.

EXAMPLE 4

The cDNA for HLA-35 had been obtained fro m cells of LB1047-RCC previously. A CDNA library was also prepared, from BB49-SCCHN The cDNA was then used to prepare recombinant plasmids, using pcDNAI/Amp, after which the plasmids were electroporated into E.coli DH5α, and selected with 50 µg/ml of ampicillin. The library was divided into 800 pools of 100 bacteria each, and each pool of bacteria was amplified to saturation. The plasmid DNA was then extracted.

The extracted cDNA was then used, in cotransfection experiments, using the previously mentioned HLA-B35 cDNA. Cotrans-fection was carried out using the well known DEAE-dextran-chloroquine method. In brief, 1.5× 10$^4$ COS-7 cells were transfected with 100 ng of recombinant plasmid pcDNAI/Amp, from the library described above, and 50 ng of plasmid pcDNA3 containing HLA-B35 cDNA. Transfectants were then tested to determine if they could stimulate TNF production by CTL clones 328a/69 and 328a/121, using the methods discussed herein. A cDNA pool was found which was positive with respect to both CTL clones, and sequenced.

Subcloning was then carried out, and individual plasmid DNA was used in the transfection and screening processes discussed above. A cDNA clone, set forth in SEQ ID NO: 1, was isolated using these procedures.

EXAMPLE 5

The isolated CDNA was then tested in cotransfection experiments, using autologous HLA-B35 CDNA, which had been cloned, by PCR. To clone the HLA-B35, the primers 5'-CGGGATCCGCCGAGATGCGGGTCAC-3' (SEQ ID NO: 2) and 5-'ACTGCCCGAATTCTCTCAGTCCCTCACAAGGCA GCTGTC-3' (SEQ ID NO: 4) were used as sense and antisense primers, respectively. The PCR was carried out for 35 cycles (one minute at 94° C., five seconds at 62° C., five minutes at 75° C. is one cycle), using the PFU polymerase enzyme. PCR product was cloned into pCDNA3, and used with the plasmids containing SEQ ID NO: 1, to cotransfect COS cells.

Figure 5:
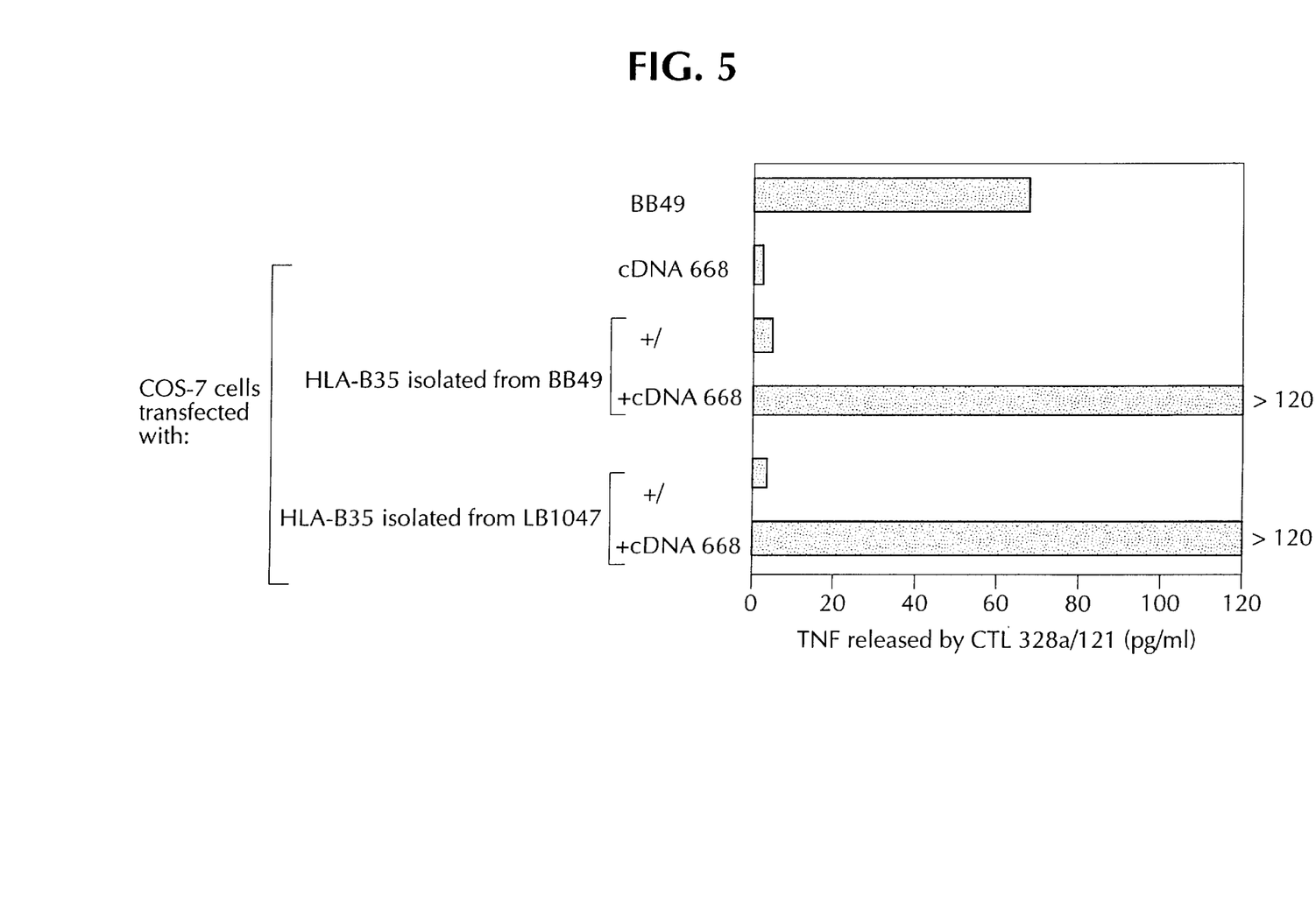
FIG. 5 shows that the CTLs identified cells which were transfected with HLA-B35, and the cDNA SEQ ID NO: 1.

As FIG. 5 shows, transfectants were recognized by the CTLs.

EXAMPLE 6

The cDNA clone discussed supra (SEQ ID NO: 1), is 2649 base pairs long. The closest homology was with a clone identified as "yyllgll.sl. Homo sapiens cDNA clone 270980", in the Genbank library. This clone, in turn, is similar to a sequence encoding cell death protein 3 ("CED-3"), as taught by Henkart, Immunity 4: 195–201 (Mar. 1996). Experiments were then carried out to determine if SEQ ID NO: 1 belonged to a family of related genes.

To test this, Southern blotting was carried out using DNA extracted from blood lymphocytes and tumor cells of patient BB49. The DNA was digested with EcoRI or HindIII. DNA capillary transfer was then carried out on membranes, using alkaline blotting. Following the transfer, the membranes were rinsed in 2xSSC, baked for one hour at 80° C., and then pretreated for 30 minutes at 60° C. in 6xSSC, and 10xDenhardt's solution. Hybridization was then carried out at 65° C. for 18 hours, in 3.5xSSC, 1xDenhardt's solution, 25 mM $NaH_2PO_4$, pH 7.0, 0.5% SDS, 2 mM EDTA, 100 μg/ml of herring sperm DNA, and $^{32}$P labelled nucleotides 1158–1482 of SEQ ID NO: 1, which was produced via PCR. The membrane was washed twice, for 30 minutes each time, at 65° C. in 2xSSC, 0.5% SDS, then twice for 30 minutes in 0.2xSSC 0.1% SDS, and once for five minutes in 0.1xSSC, 0.1% SDS. Autoradiography was carried out for three days.

Only one, approximately 5 kb band was observed with EcoRI digestion, and only one approximately 4 kb band was observed following HindIII digestion. This suggests that the isolated sequence does not belong to a family of related genes.

Lack of homology at the nucleotide level, however, is characteristic of the family of molecules known as the ICE cysteine proteases. Indeed, the deduced amino acid sequence for SEQ ID NO: 1 shows 21% homology with one such protein, i.e., CPP32, including the motif "QACXG" (SEQ ID NO: 5), wherein "X" is generally R. Support for X being Q comes from the deduced amino acid sequence for SEQ ID NO: 1, wherein X is Q. This position is supported by Fernandes-Alnermi et al., Proc. Natl. Acad. Sci. USA 93: 7464–7469 (1996), incorporated by reference. This paper describes two newly identified members of the cysteine protease family, i.e., mch 4 and mch 5, both of which have "Q" at the relevant position. Also see Henkart, Immunity 4: 195–201 (Mar. 1996), incorporated by reference. The ICE cysteine proteases are associated with cellular apoptosis, suggesting that the protein encoded by the nucleic acid molecule may be associated with apoptosis.

EXAMPLE 7

The region of SEQ ID NO: 1 which encodes the antigenic peptide was determined. To do this, deletions of the sequence were carried out from the 3' end of the clone, using commercially available exonucleaseIII. Plasmids containing the truncated cDNA were then cotransfected into COS-7 cells, together with autologous HLA-B35 cDNA, and the cotransfectants were then tested for CTL recognition in a TNF production assay. When the longest negative clone (nucleotides 1–1446), was compared to the shortest positive clone (nucleotides 1–1600), it was clear that at least the C-terminus of the antigenic peptide was encoded within nucleotides 1447–1600.

EXAMPLE 8

The identification of nucleotides 1447–1600 of the cDNA as encoding a peptide which included a tumor rejection antigen within it led to further investigations. First, the amino acid sequence corresponding to this nucleotide sequence was deduced. Next, the deduced amino acid sequence was studied to determine if any consensus sequences for peptide binding to HLA-B35, as provided by Ramensee et al., Immunogenetics 41: 178–229 (1995), were present. The consensus sequence for such binding requires PRo at position 2, and a hydrophobic residue (Tyr, Phe, Met, Leu or Ile), at the C-terminus. The following peptides were found to be included within the deduced amino acid sequence:

Phe Pro Ser Asp Ser Trp Cys Tyr Phe (SEQ ID NO: 2) and
Phe Pro Ser Asp Ser Trp Cys Tyr (SEQ ID NO: 6)

Both peptides were synthesized using well known solid phase methodologies. They were then used in a well known $^{51}$Cr release assay, to determine if they could induce lysis of target cells by CTLs. Specifically, target cells were labelled with $^{51}$Cr, for one hour, at 37° C., and washed extensively. Groups of 1000 cells were incubated with various concentrations of peptides, for 30 minutes at 37° C. Then, 10,000 CTLs were added, and $^{51}$Cr release was measured, four hours later.

Figure 6:
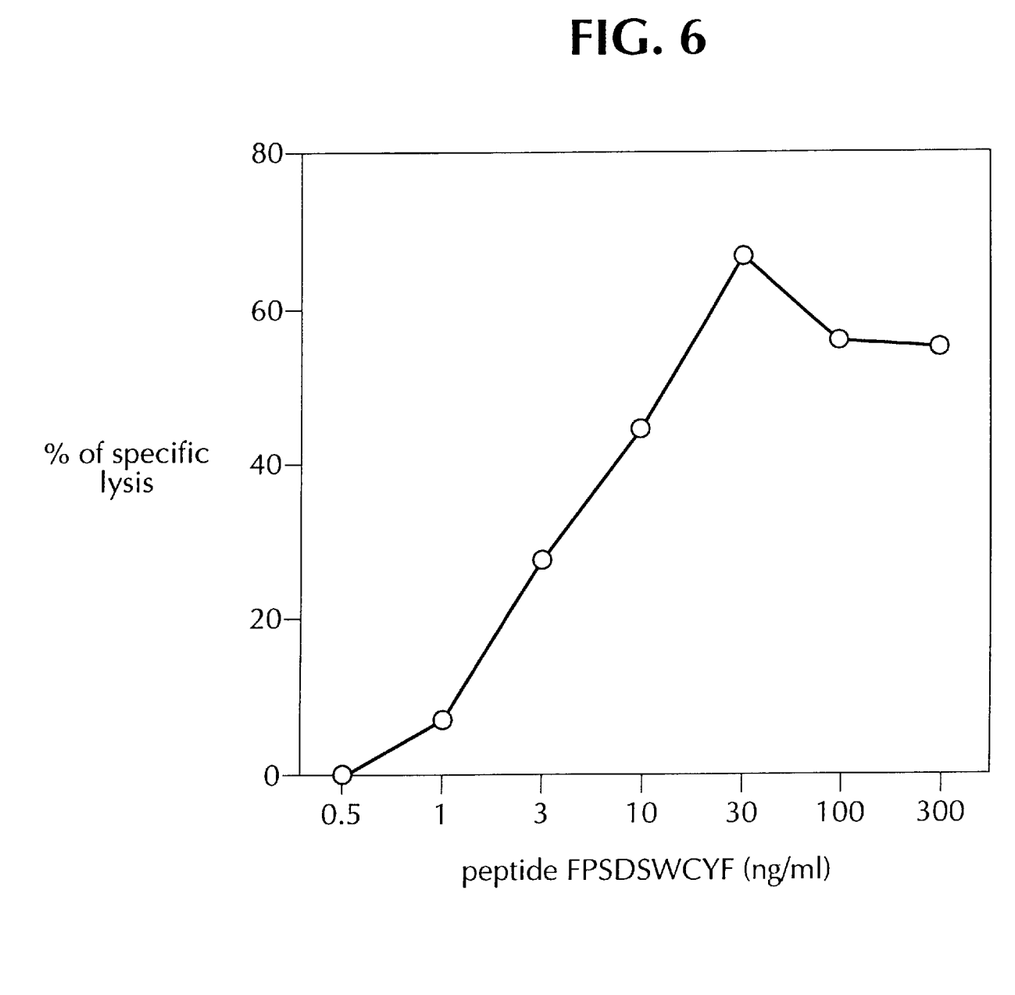
FIG. 6 depicts $^{51}$Cr assays performed using SEQ ID NO: 2.

As FIG. 6 shows, the nonamer did provoke lysis. Data for the octamer are not shown, as the octamer did not induce $^{51}$Cr release.

EXAMPLE 9

Comparison of SEQ ID NO: 1 with yyllgll.sl, discussed in example 6, supra, suggested that SEQ ID NO: 1 may have a mutated stop codon at positions 1507–1509. Furthermore, in papers published by Boldin et al., Cell 85: 803–815 (Jun. 14, 1996) and Muzio et al, Cell 85: 817–827 (Jun. 14, 1996), a protein is disclosed, named "MACH" by Boldin et al., and FLICE by Muzio et al. The amino acid sequence disclosed in these papers corresponds to an amino acid sequence encoded by nucleotides 70–1507 of SEQ ID NO: 1. The open reading frame encoded within the nucleotide sequence of SEQ ID NO: 1, however, is much longer than this, suggesting a stop codon mutation.

To investigate this issue, RNA was isolated from a surgical sample taken from BB49-SCCHN, following standard methodologies. The RNA was then subjected to RT-PCR using primers consisting of nucleotides 683–703 (sense) and 1510–1530 (antisense) of SEQ ID NO: 1. The RT-PCR was carried out for five minutes at 95° C., followed by 30 cycles (one cycle: 1 minute at 95° C., 2 minutes at 55° C., and 2 minutes at 72° C.), followed by an additional 15 minutes at 72° C. The PCR product was then purified and sequenced. Specifically, a sequencing primer consisting of nucleotides 1423–1443 of SEQ ID NO: 1 was labelled by combining 10 pmols of primer (from 4 μM of stock solution) with 5 pmol of $\gamma^{33}$ P-ATP, 0.5 μl of 10xkinase buffer (70 mM Tris-HCl, 10 mM $MgCl_2$, 5 mM DTT), pH 7.6, and 10 units of T4 polynucleotide kinase. Water was added to bring the volume to 5 μl. The mixture was incubated for 45 minutes at 37° C., after which 15 μl of water were added.

Following this reaction, 200 ng of the PCR product were used in a sequencing reaction. Specifically 11.5 μl of PCR product were combined with 2.0 μl of standard reaction buffer, and 2.0 μl of labelled primer (described supra). A sample of DNA polymerase (2.0 μl), was also added. A 4 μl portion of this mixture was added to each of 4 tubes, to which was also added 4 ul of one of four termination mixtures. Each termination mixture contained 150 μM of each of DATP, dCTP, dTTP, and 7-deaza dGTP. Each mixture contained 1.5 μM of one of d dATP ddCTP, ddGTP, or ddTTP.

The tubes were then placed in a thermocycler, and subjected to amplification. Specifically, the amplification began by cycling for 5 minutes at 95° C., followed by 49 iterations of a cycle of 30 seconds at 95° C., 1 minute at 53° C., and 2 minutes at 94° C. Reactions were halted by adding 4 μl of stop reactant (95% formamide, 20 mM EDTA, 0.05% bromophenol blue, and 0.05% xylene cyanol FF). A total of 3 ul of each amplified PCR product was then denatured for 2 minutes at 95° C., and then loaded into a denaturing gel.

The results indicated that two alleles were present. One allele contained a mutation at position 1508, with "G" being mutated to "C", as compared to the yyllgll.sl sequence, and confirmed by the sequences set forth in the Boldin and Muzio papers. This results in the elimination of a stop codon (i.e., triplet TGA becomes TCA), resulting in an extensive increase in the size of the open reading frame to a new stop codon at positions 1771–1773.

The same experiments were carried out on two other samples from BB49-PBL and BB49-EBV, and the mutation was not observed. Analysis of genomic DNA from BB49-SCCHN showed both the normal "G" and mutated "C" alleles.

These results suggest that cellular apoptosis may be affected via the presence or absence of the protein expressed from the longer open reading frame. This may be a result of, e.g., a change in balance of levels of normal and mutated proteins, and/or some type of competition between normal and mutated protein, wherein the mutated protein reduces the normal rate of apoptosis, thereby increasing cell survival and proliferation, which is characteristic of tumor cells.

The foregoing examples describe the identification of the nonapeptide of SEQ ID NO: 2 as a tumor rejection antigen which binds to and is presented by cells which present HLA-B35 on their surfaces. Thus, this peptide serves, inter alia, as a "marker" for HLA-B35 positive cells, as one can study its binding or lack thereof, to target cells, to determine their HLA type. The peptide can be used, e.g., in labelled or unlabelled form, using well known assay techniques.

As has been shown, the complexes of SEQ ID NO: 2 and HLA-B35 provoke proliferation of CTLs against these complexes. Isolated CTL's against these complexes are another feature of this invention, as is the use of these CTLs, both therapeutically and diagnostically. For example, one can determine presence of HLA-B35 cells in a sample by contacting the sample with such CTLs, and then observing, e.g., either TNF release, target cell lysis, and so forth, as an indicia of the presence of said cells, Similarly, subjects who are afflicted with disorders characterized by complexes of SEQ ID NO: 2 and HLA-B35 can be treated via administration of such CTLs.

Further, one can eliminate HLA-B35 cells from a sample and/or subject via administration of the peptide of SEQ ID NO: 2, as it has been shown that SEQ ID NO: 2 binds and form complexes with HLA-B35, and provokes lysis of the cell(s) to which it binds, via CTLs.

The invention also encompasses the isolated nucleic acid molecule of SEQ ID NO: 1, as well as a fragment thereof, which consists of nucleotides 1447–1600. Each of these molecules, as has been shown, encodes a tumor rejection antigen, i.e., that of SEQ ID NO: 2. Also encompassed by the invention are nucleic acid molecules which encode SEQ ID NO: 2, as well as isolated nucleic acid molecules which hybridize to SEQ ID NO: 1, or the 1447–1600 nucleotide fragment thereof under stringent conditions. While these conditions may vary, stringency of at least 0.2×SSC, 0.1% SDS at 65° C. is required. Also a part of the invention are expression vectors which comprise any of the foregoing sequences, operably linked to a promoter, as well as cells, i.e., prokaryotic or eukaryotic cells, transformed or transfected with the listed nucleic acid molecules and/or expression vectors.

The mutation in the stop codon has several ramifications which are a part of the invention. It will be clear to the skilled artisan that the change in the open reading frame results in a protein being encoded which is larger than the normally occurring protein. The added sequence is of sufficient size to render it immunogenic, thereby permitting the artisan to generate antibodies specific for the mutated, apoptotic protein (i.e., amino acids encoded by nucleotides 1507–1773). This enables the artisan to run assays, such as immunoassays, to determine apoptotic status of a cell or cell containing sample. Such an assay is valuable in the context of, e.g., therapies where change in status of apoptosis is desired be it a decrease, or increase in the rate. Further, primers, such as nucleotides 1423–1443 of SEQ ID NO: 1 can be used, in standard hybridization assays, to detect presence or absence of a mutated allele. Further, the fact that the mutation is a single base makes it possible to consider therapeutic methodologies where, e.g., homologous recombination or other nucleotide based therapies can be used.

Other aspects of the invention will be clear to the skilled artisan, and need not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated cytolytic T cell line which is specific for complexes of SEQ ID NO: 2 and HLA-B35.

2. Method for determining that a sample contains HLA-B35 positive cells, comprising contacting said sample with the peptide defined by SEQ ID NO: 2 in an amount sufficient to form sufficient complexes of said peptide and HLA-B35 molecules to stimulate activity of cytolytic T cells specific for said complexes, and with the cytolytic T cell of claim 1, and determining activity of said cytolytic T cell as a determination of HLA-B35 positive cells in said sample.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
    (A) LENGTH: 2649 base pairs
    (B) TYPE: nucleic acid
    (C) STRANDEDNESS: double
    (D) TOPOLOGY: linear (xi) SEQUENCE DESCRIPTION: SEQ ID NO: 1:

| | | | | | |
|---|---|---|---|---|---|
| GTGGATAGGC | CTGTGACGAA | GGTGCTACCA | TCGTGAGAGT | AAGATTATAT | TCTCCTGCCT | 60 |
| TTTAAAAAGA | TGGACTTCAG | CAGAAATCTT | TATGATATTG | GGAACAACT | GGACAGTGAA | 120 |
| GATCTGGCCT | CCCTCAAGTT | CCTGAGCCTG | GACTACATTC | CGCAAAGGAA | GCAAGAACCC | 180 |
| ATCAAGGATG | CCTTGATGTT | ATTCCAGAGA | CTCCAGGAAA | AGAGAATGTT | GGAGGAAAGC | 240 |
| AATCTGTCCT | TCCTGAAGGA | GCTGCTCTTC | CGAATTAATA | GACTGGATTT | GCTGATTACC | 300 |
| TACCTAAACA | CTAGAAAGGA | GGAGATGGAA | AGGGAACTTC | AGACACCAGG | CAGGGCTCAA | 360 |
| ATTTCTGCCT | ACAGGGTCAT | GCTCTATCAG | ATTTCAGAAG | AAGTGAGCAG | ATCAGAATTG | 420 |
| AGGTCTTTTA | AGTTTCTTTT | GCAAGAGGAA | ATCTCCAAAT | GCAAACTGGA | TGATGACATG | 480 |
| AACCTGCTGG | ATATTTTCAT | AGAGATGGAG | AAGAGGGTCA | TCCTGGGAGA | AGGAAAGTTG | 540 |
| GACATCCTGA | AAAGAGTCTG | TGCCCAAATC | AACAAGAGCC | TGCTGAAGAT | AATCAACGAC | 600 |
| TATGAAGAAT | TCAGCAAAGA | GAGAAGCAGC | AGCCTTGAAG | GAAGTCCTGA | TGAATTTTCA | 660 |
| AATGGGGAGG | AGTTGTGTGG | GGTAATGACA | ATCTCGGACT | CTCCAAGAGA | ACAGGATAGT | 720 |
| GAATCACAGA | CTTTGGACAA | AGTTTACCAA | ATGAAAAGCA | AACCTCGGGG | ATACTGTCTG | 780 |
| ATCATCAACA | ATCACAATTT | TGCAAAAGCA | CGGGAGAAAG | TGCCCAAACT | TCACAGCATT | 840 |
| AGGGACAGGA | ATGGAACACA | CTTGGATGCA | GGGGCTTTGA | CCACGACCTT | TGAAGAGCTT | 900 |
| CATTTTGAGA | TCAAGCCCCA | CGATGACTGC | ACAGTAGAGC | AAATCTATGA | GATTTTGAAA | 960 |
| ATCTACCAAC | TCATGGACCA | CAGTAACATG | GACTGCTTCA | TCTGCTGTAT | CCTCTCCCAT | 1020 |
| GGAGACAAGG | GCATCATCTA | TGGCACTGAT | GGACAGGAGG | CCCCCATCTA | TGAGCTGACA | 1080 |
| TCTCAGTTCA | CTGGTTTGAA | GTGCCCTTCC | CTTGCTGGAA | AACCCAAAGT | GTTTTTTATT | 1140 |
| CAGGCTTGTC | AGGGGGATAA | CTACCAGAAA | GGTATACCTG | TTGAGACTGA | TTCAGAGGAG | 1200 |
| CAACCCTATT | TAGAAATGGA | TTTATCATCA | CCTCAAACGA | GATATATCCC | GGATGAGGCT | 1260 |
| GACTTTCTGC | TGGGGATGGC | CACTGTGAAT | AACTGTGTTT | CCTACCGAAA | CCCTGCAGAG | 1320 |
| GGAACCTGGT | ACATCCAGTC | ACTTTGCCAG | AGCCTGAGAG | AGCGATGTCC | TCGAGGCGAT | 1380 |
| GATATTCTCA | CCATCCTGAC | TGAAGTGAAC | TATGAAGTAA | GCAACAAGGA | TGACAAGAAA | 1440 |
| AACATGGGGA | AACAGATGCC | TCAGCCTACT | TTCACACTAA | GAAAAAAACT | TGTCTTCCCT | 1500 |
| TCTGATTCAT | GGTGCTATTT | TGTTTGTTTT | GTTTTGTTTT | GTTTTTTTGA | GACAGAATCT | 1560 |
| CGCTCTGTCG | CCCAGGCTGG | AGTGCAGTGG | CGTGATCTCG | GCTCACCGCA | ACGTCCGCCT | 1620 |
| CCCGGGTTCA | CGCCATTCTC | CTGCCTCAGC | CTCCCGAGTA | GCTGGGACTA | CAGGGGCCCG | 1680 |
| CCACCACACC | TGGCTAATTT | TTTAAAAATA | TTTTTAGTAG | AGACAGGGTT | TCACTGTGTT | 1740 |
| AGCCAGGGTG | GTCTTGATCT | CCTGACCTCG | TGATCCACCC | ACCTCGGCCT | CCCAAAGTGC | 1800 |
| TGGGATTACA | GGCGTGAGCC | ACCGCGCCTG | GCCGATGGTA | CTATTTAGAT | ATAACACTAT | 1860 |
| GTTTATTTAC | TAATTTTCTA | GATTTTCTAC | TTTATTAATT | GTTTTGCACT | TTTTTATAAG | 1920 |
| AGCTAAAGTT | AAATAGGATA | TTAACAACAA | TAACACTGTC | TCCTTTCTCT | TATGCTTAAG | 1980 |
| GCTTTGGGAA | TGTTTTTAGC | TGGTGGCAAT | AAATACCAGA | CACGTACAAA | ATCCAGCTAT | 2040 |
| GAATATAGAG | GGCTTATGAT | TCAGATTGTT | ATCTATCAAC | TATAAGCCCA | CTGTTAATAT | 2100 |
| TCTATTAACT | TTAATTCTCT | TTCAAAGCTA | AATTCCACAC | TACCACATTA | AAAAAATTAG | 2160 |

```
AAAGTAGCAC GTATGGTGGC TCATGTCTAT AATCCCAGCA CTTTGGGAGG TTGAGGTGGG    2220

AGGATTGCTT GAACCCAAGA GGTCAAGGCT GCAGTGAGCC ATGTTCACAC CGCTGCACTC    2280

AGGCTTGGGT GACAGAACAA GACCCCGTCT CAAAAAAAAT TTTTTTTTTA ATAAAACAAA    2340

ATTTGTTTGA AAACTTTTAA AAATTCAAAT GATTTTTACA AGTTTAAAT AAGCTCTCCC     2400

CAAACTTGCT TTATGCCTTC TTATTGCTTT TATGATATAT ATATGCTTGG CTAACTATAT    2460

TTGCTTTTTG CTAACAATGC TCTGGGGTCT TTTTATGCAT TTGCATTTGC TCTTTCATCT    2520

CTGCTTGGAT TATTTTAAAT CATTAGGAAT TAAGTTATCT TTAAAATTTA AGTATCTTTT    2580

TTCAAAAACA TTTTTTAATA GAATAAAATA TAATTTGATC TTAAAAAAAA AAAAAAAAA    2640

AAAAAAAAA                                                             2649
```

(2) INFORMATION FOR SEQ ID NO: 2:

(i) SEQUENCE CHARACTERISTICS:
        (A) LENGTH: 9 amino acids
        (B) TYPE: amino acid
        (D) TOPOLOGY: linear     (ii) MOLECULE TYPE: protein     (xi) SEQUENCE DESCRIPTION: SEQ ID NO: 2:

Phe Pro Ser Asp Ser Trp Cys Tyr Phe
              5

(2) INFORMATION FOR SEQ ID NO: 3:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear     (xi) SEQUENCE DESCRIPTION: SEQ ID NO: 3:

```
CGGGATCCGC CGAGATGCGG GTCAC                                             25
```

(2) INFORMATION FOR SEQ ID NO: 4:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear     (xi) SEQUENCE DESCRIPTION: SEQ ID NO: 4:

```
ACTGCCCGAA TTCTCTCAGT CCCTCACAAG GCAGCTGTC                              39
```

(2) INFORMATION FOR SEQ ID NO: 5:

(i) SEQUENCE CHARACTERISTICS:
        (A) LENGTH: 5 amino acids
        (B) TYPE: amino acid
        (D) TOPOLOGY: linear     (ii) MOLECULE TYPE: protein     (xi) SEQUENCE DESCRIPTION: SEQ ID NO: 5:

Gln Ala Cys Xaa Gly
          5

(2) INFORMATION FOR SEQ ID NO: 6:

(i) SEQUENCE CHARACTERISTICS:
        (A) LENGTH: 8 amino acids

```
        (B) TYPE: amino acid
        (D) TOPOLOGY:  linear (ii) MOLECULE TYPE:  protein (xi) SEQUENCE DESCRIPTION: SEQ ID NO: 6:

Phe Pro Ser Asp Ser Trp Cys Tyr
```